US008217358B2

(12) United States Patent
Liu et al.

(10) Patent No.: US 8,217,358 B2
(45) Date of Patent: Jul. 10, 2012

(54) SYSTEM AND METHOD OF ELIMINATING IMAGE ARTIFACTS

(75) Inventors: James Zhengshe Liu, Glenview, IL (US); Feng Gao, Naperville, IL (US); Kenneth Scott Kump, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 88 days.

(21) Appl. No.: 12/637,069

(22) Filed: Dec. 14, 2009

(65) Prior Publication Data

US 2011/0139993 A1   Jun. 16, 2011

(51) Int. Cl.
*G01T 1/20* (2006.01)
(52) U.S. Cl. .................................................. 250/370.09
(58) Field of Classification Search ............... 250/370.09
See application file for complete search history.

(56) References Cited

U.S. PATENT DOCUMENTS

| | | | |
|---|---|---|---|
| 6,400,798 B1 | 6/2002 | Leparmentier et al. | |
| 6,538,253 B2 | 3/2003 | Petrick et al. | |
| 6,759,641 B1 | 7/2004 | Loose | |
| 7,119,341 B2 | 10/2006 | Petrick | |
| 7,495,228 B1 | 2/2009 | Albagli et al. | |
| 2002/0085670 A1* | 7/2002 | Vafi et al. | 378/98.8 |
| 2005/0121616 A1 | 6/2005 | Petrick | |
| 2008/0296507 A1 | 12/2008 | Petrick et al. | |
| 2010/0119140 A1* | 5/2010 | Burns et al. | 382/132 |

* cited by examiner

*Primary Examiner* — David Porta
*Assistant Examiner* — Casey Bryant
(74) *Attorney, Agent, or Firm* — Fletcher Yoder, P.C.

(57) ABSTRACT

A system and method for eliminating image artifacts caused by electromagnetic interference (EMI) on a digital x-ray detector. The system and method includes a digital x-ray detector panel having an array of pixels in rows and columns, with a plurality of data lines coupled to the columns of pixels and a plurality of scan lines coupled to the rows of pixels. The system and method uses certain photodiodes in a row of the pixel array for measuring EMI with corresponding scan line and FETs deactivated and eliminating the EMI and image artifacts with the remaining photodiodes in the row with corresponding scan line and FETs activated.

19 Claims, 5 Drawing Sheets

SYSTEM AND METHOD OF ELIMINATING IMAGE ARTIFACTS

BACKGROUND OF THE INVENTION

This disclosure relates generally to x-ray imaging systems, and more particularly to techniques for correcting the effects of electromagnetic interference (EMI) on image data acquired with such x-ray imaging systems.

A number of x-ray imaging systems of various designs are known and are presently in use. Such systems generally are based upon generation of x-rays that are directed toward a subject of interest. The x-rays traverse the subject and impact a film or a digital detector. Increasingly, such x-ray imaging systems use digital circuitry for detecting the x-rays, which are attenuated, scattered or absorbed by the intervening structures of the subject. In medical imaging contexts, for example, such systems may be used to visualize the internal structures, tissues and organs of a subject for the purpose of screening or diagnosing patient ailments. In other contexts, parts, structures, baggage, parcels, and other subjects may be imaged to assess their contents, structural integrity or other purposes.

In the field of diagnostic imaging, digital x-ray detectors are gradually replacing film cassettes. Digital x-ray detectors generally provide better image quality and improved processing time, image storage and image transfer over previously known x-ray film techniques. However, digital x-ray detectors are susceptible to EMI. The EMI may create artifacts in the x-ray images.

Sources of EMI may include, for example, various electrical and electronic equipment and systems used in the vicinity of the digital x-ray detectors. Temporally and spatially changing electromagnetic fields can induce phantom signals in the digital x-ray detector that show up as image artifacts in an acquired image. Depending upon the phase, frequency and amplitude of the EMI, artifacts in the reconstructed images may generally take the form of darker and lighter parallel rows superimposed on the basic image. Such artifacts are not only distracting, but may impair effective use of the images, such as for diagnosis in a medical context. In particular, such artifacts may make small or more detailed features that would otherwise be visible in the images, difficult to detect. These image artifacts can degrade the overall image quality of a digital x-ray imaging system. Although shielding can be used to attenuate the amplitude of the electromagnetic radiation, this shielding will also attenuate the x-ray radiation and degrade the overall image quality of the x-ray imaging system.

Therefore, there is a need for a digital x-ray imaging system having a digital x-ray detector with reduced sensitivity to EMI that produces high quality images with no artifacts.

BRIEF DESCRIPTION OF THE INVENTION

In accordance with an aspect of the present disclosure, a digital x-ray detector comprising a pixel array with a plurality of pixels arranged in rows and columns; a scan line coupled to each pixel in a row; and a data line coupled to each pixel in a column; wherein the scan line is separated into a first scan line coupled to even pixels in a row and a second scan line coupled to odd pixels in the row.

In accordance with another aspect of the present disclosure, a system for eliminating image artifacts caused by electromagnetic interference (EMI) on a digital x-ray detector comprising a pixel array with a plurality of pixels arranged in rows and columns; a scan line coupled to each pixel in a row; and a data line coupled to each pixel in a column; wherein the scan line is separated into a first scan line coupled to even pixels in a row and a second scan line coupled to odd pixels in the row.

In accordance with a further aspect of the present disclosure, a method for eliminating image artifacts caused by EMI on a digital x-ray detector comprising acquiring image and EMI signal data during an x-ray image acquisition; activating a plurality of first scan lines coupled to even pixels in rows of a pixel array of a digital x-ray detector panel to measure the x-ray image signal of the even pixels in the rows; deactivating a plurality of second scan lines coupled to odd pixels in the row of the pixel array of the digital x-ray detector panel to measure the EMI signal of the odd pixels in the rows; removing the EMI signal from the even pixels with the measured EMI signal from the odd pixels; activating the plurality of second scan lines coupled to the odd pixels in the rows of the pixel array of the digital x-ray detector panel to measure the x-ray image signal of the odd pixels in the rows; deactivating the plurality of first scan lines coupled to the even pixels in the rows of the pixel array of the digital x-ray detector panel to measure the EMI signal of the even pixels in the rows; and removing the EMI signal from the odd pixels with the measured EMI signal from the even pixels.

Various other features, aspects, and advantages will be made apparent to those skilled in the art from the accompanying drawings and detailed description thereof.

DETAILED DESCRIPTION OF THE INVENTION

Figure 1:
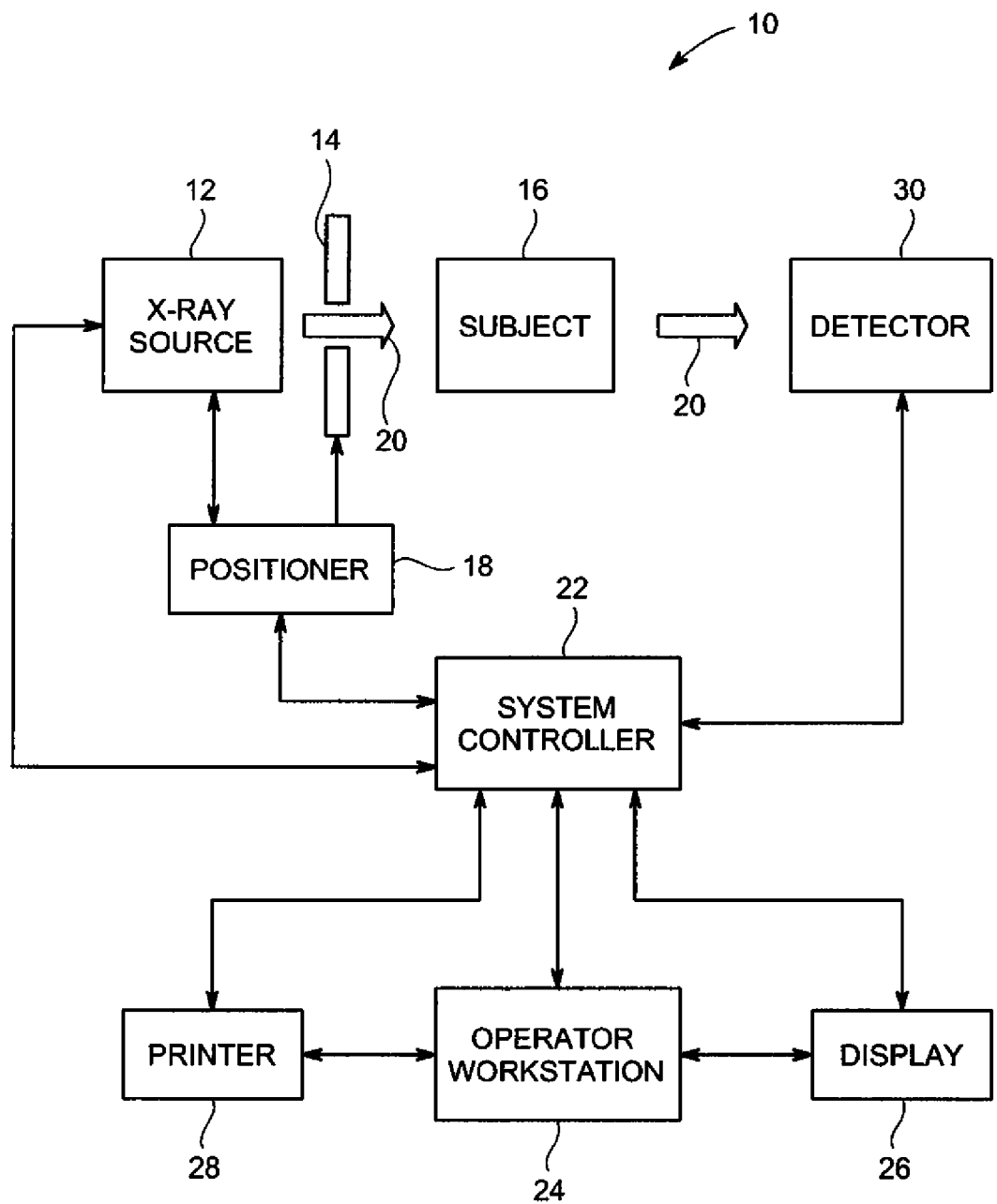
FIG. 1 is a block diagram of an exemplary embodiment of a digital x-ray imaging system.

Referring to the drawings, FIG. 1 illustrates a block diagram of an exemplary embodiment of a digital x-ray imaging system 10. The digital x-ray imaging system 10 includes an x-ray source 12, a collimator 14 adjacent to the x-ray source 12, a subject 16 to be imaged, a digital x-ray detector 30, and a positioner 18. The positioner 18 is a mechanical controller coupled to x-ray source 12 and collimator 14 for controlling the positioning of x-ray source 12 and collimator 14.

The digital x-ray imaging system 10 is designed to create images of the subject 16 by means of an x-ray beam 20 emitted by x-ray source 12, and passing through collimator 14, which forms and confines the x-ray beam 20 to a desired region, wherein the subject 16, such as a human patient, an animal or an object, is positioned. A portion of the x-ray beam 20 passes through or around the subject 16, and being altered by attenuation and/or absorption by tissues within the subject 16, continues on toward and impacts the digital x-ray detector 30. In an exemplary embodiment, the digital x-ray detector 30 may be a fixed detector or a portable detector. In an exemplary embodiment, the digital x-ray detector 30 may be a digital flat panel x-ray detector. The digital x-ray detector 30 converts x-ray photons received on its surface to lower energy light photons, and subsequently to electric signals, which are acquired and processed to reconstruct an image of internal anatomy within the subject 16. The digital x-ray detector 30 is designed to eliminate electromagnetic interference (EMI) and prevent artifacts from forming on the x-ray images.

The digital x-ray imaging system 10 further includes a system controller 22 coupled to x-ray source 12, positioner 18, and digital x-ray detector 30 for controlling operation of the x-ray source 12, positioner 18, and digital x-ray detector 30. The system controller 22 may supply both power and control signals for imaging examination sequences. In general, system controller 22 commands operation of the x-ray system to execute examination protocols and to process acquired image data. The system controller 22 may also include signal processing circuitry, based on a general purpose or application-specific computer, associated memory circuitry for storing programs and routines executed by the computer, as well as configuration parameters and image data, interface circuits, and so forth.

The system controller 22 may further include at least one processor designed to coordinate operation of the x-ray source 12, positioner 18, and digital x-ray detector 30, and to process acquired image data. The at least one processor may carry out various functionality in accordance with routines stored in the associated memory circuitry. The associated memory circuitry may also serve to store configuration parameters, operational logs, raw and/or processed image data, and so forth. In an exemplary embodiment, the system controller 22 includes at least one image processor to process acquired image data.

The system controller 22 may further include interface circuitry that permits an operator or user to define imaging sequences, determine the operational status and health of system components, and so-forth. The interface circuitry may allow external devices to receive images and image data, and command operation of the x-ray system, configure parameters of the system, and so forth.

The system controller 22 may be coupled to a range of external devices via a communications interface. Such devices may include, for example, an operator workstation 24 for interacting with the x-ray system, processing or reprocessing images, viewing images, and so forth. In the case of tomosynthesis systems, for example, the operator workstation 24 may serve to create or reconstruct image slices of interest at various levels in the subject based upon the acquired image data. Other external devices may include a display 26 or a printer 28. In general, these external devices 24, 26, 28 may be local to the image acquisition components, or may be remote from these components, such as elsewhere within a medical facility, institution or hospital, or in an entirely different location, linked to the image acquisition system via one or more configurable networks, such as the Internet, intranet, virtual private networks, and so forth. Such remote systems may be linked to the system controller 22 by any one or more network links. It should be further noted that the operator workstation 24 may be coupled to the display 26 and printer 28, and may be coupled to a picture archiving and communications system (PACS). Such a PACS might be coupled to remote clients, such as a radiology department information system or hospital information system, or to an internal or external network, so that others at different locations may gain access to image data.

The data acquired by digital x-ray imaging system 10 may be corrupted by various sources of EMI (not shown) depending upon the context in which the system 10 is used, and the devices that may surround the system 10 or be used in conjunction with it, EMI of various frequencies and amplitudes, some of which may be in phase and out of phase with the acquired data may affectively be superimposed on the acquired data as it is collected. The digital x-ray imaging system 10 allows for characterization and correction of such EMI and thus reduction of image artifacts that would otherwise be present in the image data and visible in reconstructed images based upon the data. The characterization and correction itself may be carried out in any of the foregoing circuitry, including the detector circuitry or the system controller 22. Moreover, where desired, the EMI may be characterized and corrected in a post-processing step that may be partially or entirely remote from the digital x-ray imaging system 10 itself.

Figure 2:
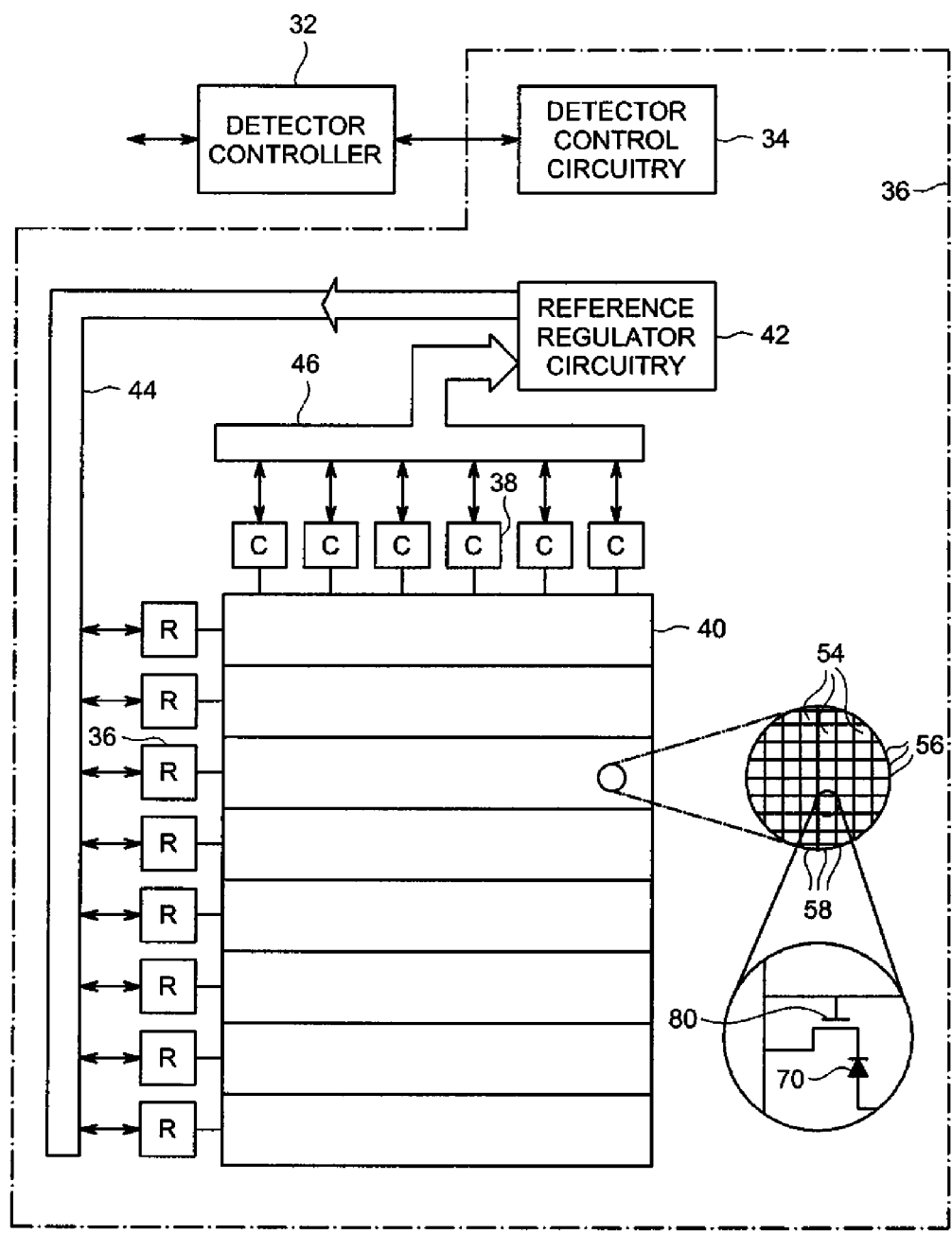
FIG. 2 is a detailed block diagram of an exemplary embodiment of the functional components of a digital x-ray detector.

FIG. 2 illustrates a detailed block diagram of an exemplary embodiment of the functional components of the digital x-ray detector 30. FIG. 2 also illustrates a detector controller 32 coupled to detector control circuitry 34 within digital x-ray detector 30 through wired or wireless communication devices and protocols. The detector controller 32 may be included within system controller 22 or may be a separate component. The detector controller 32 includes at least one processor, memory circuitry and other electronic circuitry for communicating with and controlling acquisition of images from the digital x-ray detector 30. The detector controller 32 exchanges signals and image data with the digital x-ray detector 30 during operation. The detector control circuitry 34 receives power from an internal or external power source (not shown). The detector control circuitry 34 is configured to originate timing and control commands for row electronics 36 and column electronics 38 used to acquire image data from a digital x-ray detector panel 40 during data acquisition phases of operation of the digital x-ray imaging system 10. The detector control circuitry 34 transmits power and control signals to reference/regulator circuitry 42, and in turn receives digital image data from reference/regulator circuitry 42.

Figure 3:
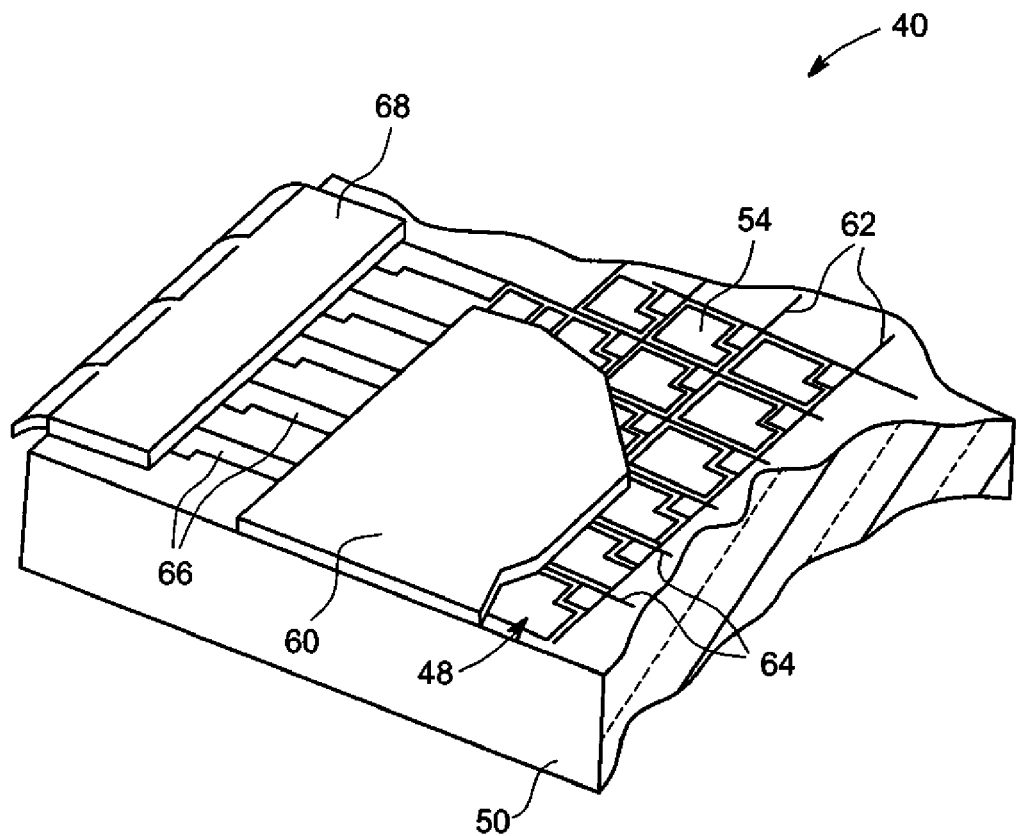
FIG. 3 is a partial sectional schematic diagram of an exemplary embodiment of a digital x-ray detector panel.

In an exemplary embodiment as shown in FIG. 3, the digital x-ray detector panel 40 comprises a glass substrate 50 on which various components are disposed. An amorphous silicon pixel array 48 including an array of light sensing photodiodes and switching thin film field effect transistors (FETs) in the same electronic circuit elements or pixels 54 is deposited on the glass substrate 50. The pixels 54 are arranged in rows and columns of the amorphous silicon pixel array 48. A scintillator material 60 is provided over the amorphous silicon pixel array 48 for receiving x-ray radiation during x-ray exposure examination sequences. Row electrodes 62 and column electrodes 64 are provided on the glass substrate 50. Contact fingers 66 are formed for communicating signals to and from the row electrodes 62 and the column electrodes 64, and contact leads 68 are provided for communicating signals between the contact fingers 66 and external circuitry. The scintillator material 60 converts incident x-ray photons received on the detector surface during examinations to lower energy light photons. The amorphous silicon pixel array 48 converts the light photons to electrical signals, which are representative of the number of light photons or the intensity of light impacting the individual pixels of the amorphous silicon pixel array 48. Readout electronics converts the resulting analog signals to digital signals that may be processed, stored and displayed following reconstruction of an image.

Returning to FIG. 2, a row bus 44 is coupled between the reference/regulator circuitry 42 and the row electronics 36 for enabling and disabling readout of the various rows of the digital x-ray detector panel 40. Similarly, a column bus 46 is coupled between the reference/regulator circuitry 42 and the column electronics 38 for enabling and disabling readout of the various columns of the digital x-ray detector panel 40, while the rows are sequentially enabled. The digital x-ray detector panel 40 forms an array of pixels 54 that are arranged in rows 56 and columns 58. Each row 56 is coupled to row electronics 36, and each column 58 is coupled to column electronics 38. As mentioned above, each pixel 54 includes a light sensing photodiode 70 and a switching FET 80 in the same electronic circuit. As each row 56 of pixels 54 in the digital x-ray detector panel 40 is enabled by row electronics 36, signals from each photodiode 70 may be accessed via readout electronics, and converted to digital signals for subsequent processing and image reconstruction.

Figure 4:
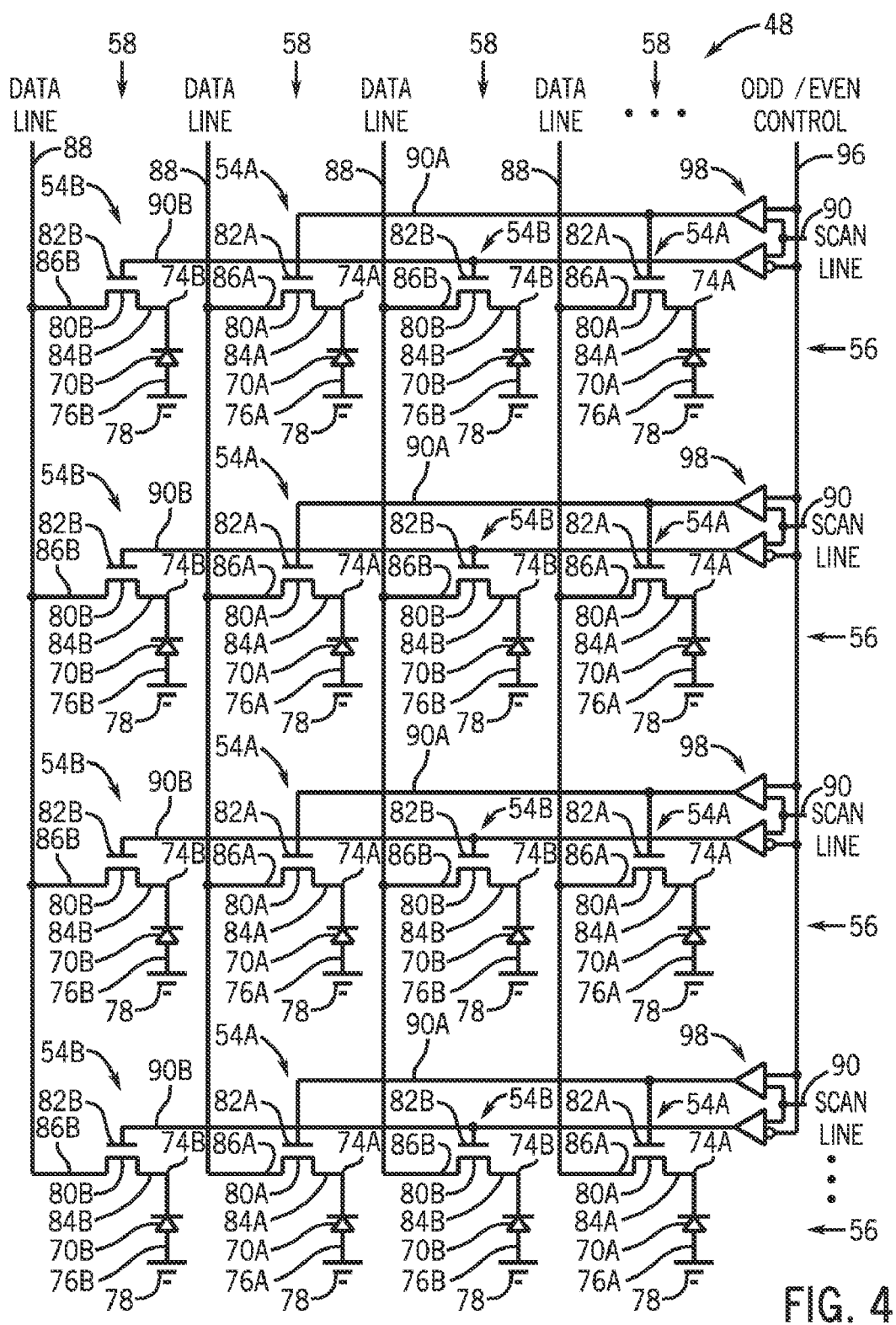
FIG. 4 is a schematic diagram of an exemplary embodiment of a pixel array of a digital x-ray detector panel.

FIG. 4 illustrates a schematic diagram of an exemplary embodiment of a pixel array 48 of a digital x-ray detector panel. The pixel array 48 includes an array of even and odd pixels 54A, 54B comprising even and odd switching FETs 80A, 80B, even and odd light detecting photodiodes 70A, 70B arranged in rows 56 and columns 58. Each row 56 is coupled to a scan line 90 and each column 58 is coupled to a data line 88.

The scan line 90 for each row 56 is separated into a first scan line 90A and a second scan line 90B, wherein the first scan line 90A is coupled to alternating pixels or every other pixel in a row 56, defined as even pixels 54A, and the second scan line 90B is coupled to the remaining alternating or every other pixel in a row 56, defined as odd pixels 54B, wherein the odd pixels 54B are adjacent to and separated by the even pixels 54A. Therefore, the even pixels 54A in a row 56 are controlled simultaneously by the first scan line 90A of the row 56, and the odd pixels 54B in a row are controlled simultaneously by the second scan line 90B of the row 56. In further detail, the first scan line 90A is coupled to a gate terminal 82A of the even FETs 80A within a row 56 and the second scan line 90B is coupled to a gate terminal 82B of the odd FETs 80B within a row 56.

Each FET 80A, 80B includes a gate terminal 82A, 82B connected to a scan line 90A, 90B, a source terminal 86A, 86B connected to a data line 88, and a drain terminal 84A, 84B connected to a cathode 74A, 74B of the photodiode 70A, 70B. The photodiode 70A, 70B also includes an anode 76A, 76B, opposite the cathode 74A, 74B that is connected to a common ground 78. The source terminals 86A, 86B of all the even or odd FETs 80A, 80B in a column are connected together and connected to a data line 88 for that column 58. The even gate terminals 82A of the even FETs 80A in a row 56 are connected together and connected to a first scan line 90A, while the odd gate terminals 82B of the odd FETs 80B in the row 56 are connected together and connected to a second scan line 90B.

The pixel array 48 further includes an odd/even control line 96 coupled to odd/even control circuitry 98 coupled to each row 56 in the array 48 that operates to select between activating the first scan line 90A or the second scan line 90B in a particular row 56. The scan line 90 for each row 56 is coupled to the odd/even control circuitry 98 for a particular row 56.

The scan lines 90 and odd/even control line 96 are used to control activation of the even and odd FETs 80A, 80B and to simultaneously allow the corresponding photodiodes 70A, 70B to charge. The voltage potential across the photodiodes 70A, 70B is formed by the difference in potential between the data line 88 potential and the common ground 78 potential. The photodiodes 70A, 70B store this voltage potential in the form of a charge.

The even and odd FETs 80A, 80B in a row 56 are turned on or placed in a conducting state when the first or second scan line 90A, 90B connected to the even and odd gate terminals 82A, 82B of the FETs 80A, 80B is activated. The even and odd FETs 80A, 80B in a row 56 are turned off or placed in a non-conducting state when the first or second scan line 90A, 90B connected to the even and odd gate terminals 82A, 82B of the FETs 80A, 80B is not activated.

When a scan line 90A, 90B is activated for a particular row 56, it turns on all the FETs 80A, 80B in the row 56 that are connected to the scan line 90A, 90B and x-ray image data is transferred from the associated photodiodes 70A, 70B to readout electronics for processing. The x-ray image data for an entire image is read out by sequentially reading out all the rows 56 of the pixel array 48.

The data line 88 for each column 58 is coupled to the even 86A or odd 86B source terminals of the even 80A or odd 80B FETs. The data lines are used to access x-ray image exposure data from the photodiodes 70 (by measuring the charge discharged by the photodiodes). This data is transmitted to readout electronic(s) circuitry to read the amount of charge discharged from the photodiodes. The photodiodes 70 are then restored to their initial charge.

Each photodiode 70A, 70B operate as charge collectors, and each FET 80A, 80B operate as switches to access the associated photodiode 70A, 70B. A readout command generated by the detector controller 32 is used to readout all x-ray image data following an x-ray exposure, and resets the charge on all photodiodes 70A, 70B in the array 48 awaiting the next x-ray exposure. When no x-ray exposure is made for an extended period of time, the detector controller 32 may generate a scrub command to reset the charge on the photodiodes 70A, 70B.

When a positive voltage is applied to the gate terminals 82A, 82B, the FETs 80A, 80B turn on and current flows from the data lines 88 to the photodiodes 70A, 70B. The charge of the corresponding photodiode 70A, 70B may be measured by readout electronics through the data lines 88 coupled to the source terminals 86A, 86B of the FETs 80A, 80B in a column 58 and converted to a digital value by an analog-to-digital converter coupled to each column 58, and the photodiodes 70A, 70B are restored to an initial charge. When a negative voltage is applied to the gate terminals 82A, 82B, the FETs 80A, 80B turn off and the photodiodes 70A, 70B are disconnected from the data lines 88.

It has been determined that EMI is picked-up in a digital x-ray detector panel by the data lines and data modules. The EMI is not affected by the status of the scan lines. In other words, image artifacts due to EMI are the same whether the scan lines are activated or not, and the EMI gets picked-up whether the FETs are on (conducting) or off (not conducting). The EMI signal (amplitude, frequency, phase) is the same no matter if scan lines are activated or not. The EMI may change as you move across a row of the digital x-ray detector panel. This means that the EMI may be different at different data lines. Also, EMI (amplitude, frequency, phase) may vary with time. Therefore, in order to eliminate image artifacts due to EMI, the EMI must be measured at the same time as the x-ray signal and must be measured over the entire pixel array of the digital detector panel.

The combination of the x-ray image signal pixel values and the EMI signal pixel values may be identified by the following equation:

$$p_{i,j}(t)=s_{i,j}(t)+n_{i,j}(t). \qquad \text{Equation (1)}$$

where $p_{i,j}(t)$ is the total pixel values measured, $s_{i,j}(t)$ is the pixel values measured of the x-ray image signal and $n_{i,j}(t)$ is the pixel values measured of the EMI signal. The pixel values are represented by whole numbers.

Let $n_j(t)$ denote the pixel values of the EMI signal obtained on data line j with the scan line i deactivated at time t. From the above discussion:

$$n_{i,j}(t)=n_j(t).\qquad\text{Equation (2)}$$

Note that $n_j(t)$ is a function of j and t, but independent of i since it is obtained with the scan line i deactivated.

By replacing $n_{i,j}(t)$ in equation (1) with equation (2), equation (1) can be rewritten as:

$$p_{i,j}(t)=s_{i,j}(t)+n_j(t).\qquad\text{Equation (3)}$$

Equation (3) illustrates that the EMI may be removed if $n_j(t)$ for data line j at time t is known when $p_{i,j}(t)$ is measured. A problem is that $p_{i,j}(t)$ and $n_j(t)$ cannot be obtained at the same time. Fortunately, the signals between two neighboring data lines are very close. Therefore, $n_{j-1}(t)$ and $n_{j+1}(t)$ may be measured, and $n_j(t)$ may be obtained through interpolation. Interpolation is defined as the average of two adjacent signal measurements between two neighboring data lines to estimate EMI (see equation 4).

Referring again to the FIG. 4, the pixel array 48 of a digital x-ray detector panel includes a first scan line 90A coupled to even pixels 54A in a row 56, and a second scan line 90B coupled to odd pixels 54B in the row 56. Therefore, the odd and even pixels 54B, 54A in a row 56 may be read separately. By reading every row 56 of pixels 54 twice with the first scan line 90A activated and the second scan line 90B deactivated, $n_j(t)$ may be obtained through interpolation. For example:

$$\hat{n}_j(t)=(n_{j-1}(t)+n_{j+1}(t))/2.\qquad\text{Equation (4)}$$

In such a way, the EMI on photodiode $d_{i,j}(t)$ may be removed by the following equation:

$$\hat{s}_j(t)=p_{i,j}(t)-\hat{n}_j(t).\qquad\text{Equation (5)}$$

Figure 5:
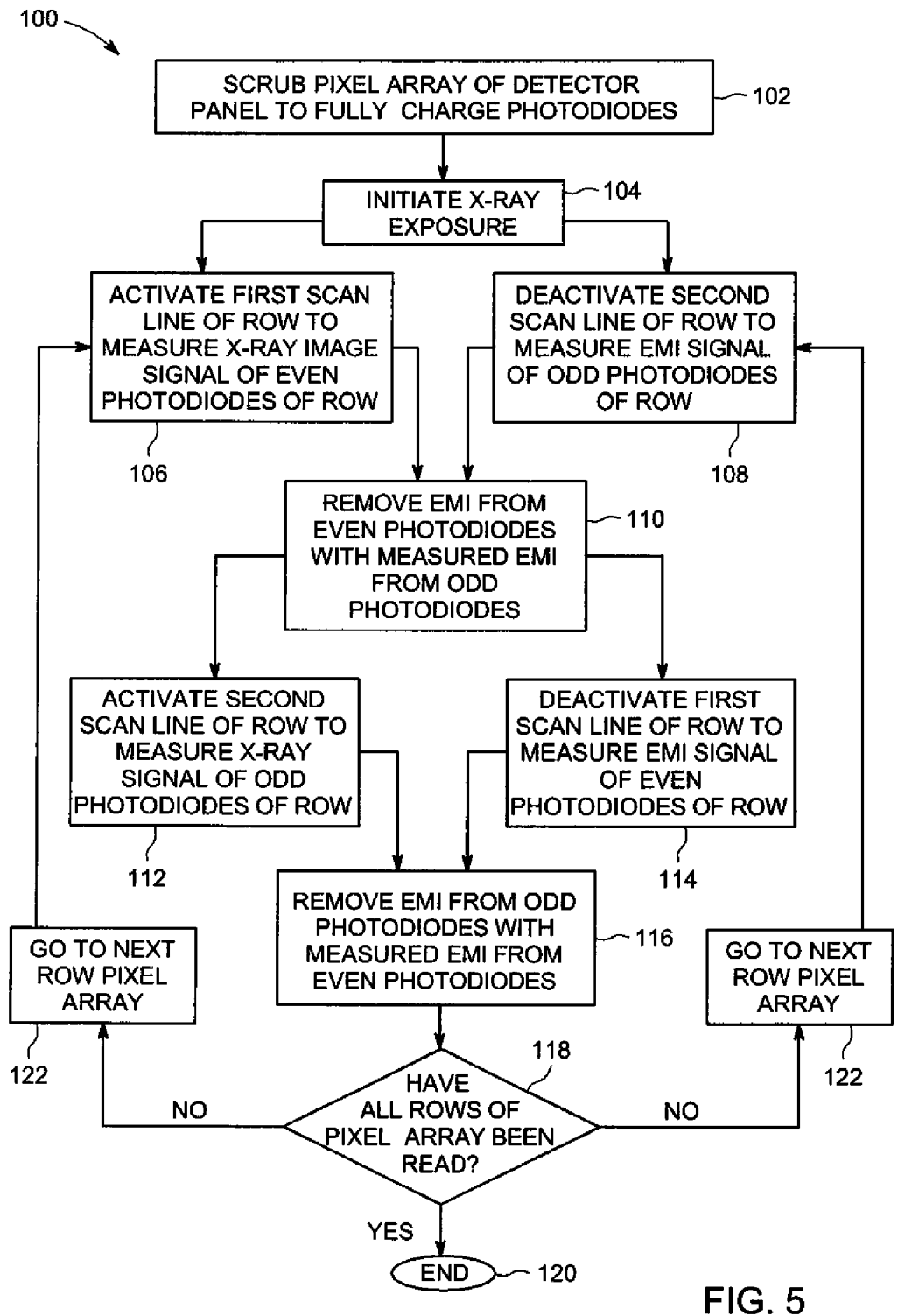
FIG. 5 is a flow diagram of an exemplary embodiment of a method of eliminating the effects of electromagnetic interference (EMI) on a digital x-ray detector.

FIG. 5 illustrates a flow diagram of an exemplary embodiment of a method 100 of eliminating the effects of EMI on a digital x-ray detector. In particular, the method 100 comprises eliminating image artifacts caused by EMI on a digital x-ray detector. The first step in the method 100 is to ensure that the charge on all photodiodes 70A, 70B in the array 48 is reset awaiting the next x-ray exposure. The detector controller 32 may generate a scrub command signal to reset the charge on the photodiodes 70A, 70B at step 102. An x-ray exposure is initiated and the photodiodes 70A, 70B are discharged based on x-ray exposure at step 104.

In order to eliminate image artifacts due to EMI, we have to obtain a reference signal that corresponds to the EMI over the entire pixel array 48 of the digital x-ray detector panel. After the x-ray exposure, every row 56 of the pixel array 48 is read twice. By reading every row 56 of pixels 54 twice, once with first scan line 90A activated and second scan line 90B deactivated to measure the image and EMI signals of the even pixels 54A and to measure the EMI signals of the odd pixels 54B, and once with first scan line 90A deactivated and second scan line 90B activated to measure the image and EMI signals of the odd pixels 54B and to measure the EMI signals of the even pixels 54A.

At step 106, the first scan line 90A of a row is activated and the x-ray image signal and EMI signal of the even pixels 54A is measured. At step 108, the second scan line 90B of the row is deactivated and the EMI signal of the odd pixels 54B is measured. The measured EMI signal from the odd pixels 54B is used to remove the EMI from the even pixels 54A at step 110.

At step 112, the second scan line 90B of the row is activated and the x-ray image signal and EMI signal of the odd pixels 54B is measured. At step 114, the first scan line 90A of the row is deactivated and the EMI signal of the even pixels 54A is measured. The measured EMI signal from the even pixels 54A is used to remove the EMI from the odd pixels 54B at step 116.

At step 118, it is determined whether all rows of pixels have been read. If not, the next step 122 is to move on to the next row 56 of the pixel array 48 and perform the same measurements and operations as discussed in steps 106, 108, 110, 112, 114 and 116 above. If the measurements and operations of all of the rows 56 of the pixel array 48 have been completed then the method is ended at step 120.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A digital x-ray detector comprising:
a pixel array with a plurality of pixels arranged in rows and columns, wherein all regions of the pixels capable of providing EMI data are also capable of providing image data;
a scan line coupled to each pixel in a row; and
a data line coupled to each pixel in a column;
wherein the scan line is separated into a first scan line coupled to even pixels in a row and a second scan line coupled to odd pixels in the row; and
circuitry coupled to the scan and data lines and configured to activate the even pixels to collect image data and EMI data from the even pixels and EMI-only data from the odd pixels, and to activate the odd pixels to collect image data and EMI data from the odd pixels and EMI-only data from the even pixels, the EMI data from the even pixels being used to correct the image and EMI data from the odd pixels, and the EMI data from the odd pixels being used to correct the image and EMI data from the even pixels.

2. The digital x-ray detector of claim 1, further comprising odd/even control circuitry coupled between the scan line and the first and second scan lines.

3. The digital x-ray detector of claim 2, further comprising an odd/even control line coupled to the odd/even control circuitry for selectively activating the first scan line or the second scan line.

4. The digital x-ray detector of claim 1, wherein each pixel includes a switching device and a photodetector device.

5. The digital x-ray detector of claim 4, wherein the switching device is a FET and the photodetector device is a photodiode.

6. The digital x-ray detector of claim 5, wherein the FET activates the photodiode to store a charge in response to a signal received by the first or the second scan line.

7. The digital x-ray detector of claim 6, wherein the pixel communicates a signal representing charge stored within the photodiode to an associated data line after selective activation of the scan line.

8. The digital x-ray detector of claim 1, wherein the first scan line is coupled to alternating pixels in a row, defined as the even pixels, and the second scan line is coupled to the remaining alternating pixels in the row, defined as the odd pixels.

9. The digital x-ray detector of claim 8, wherein the odd pixels in a row are adjacent to and separated by the even pixels in the row.

10. A system for eliminating image artifacts caused by electromagnetic interference (EMI) on a digital x-ray detector comprising:

a pixel array with a plurality of pixels arranged in rows and columns, wherein all regions of the pixels capable of providing EMI data are also capable of providing image data;

a scan line coupled to each pixel in a row; and a data line coupled to each pixel in a column;

wherein the scan line is separated into a first scan line coupled to even pixels in a row and a second scan line coupled to odd pixels in the row; and circuitry coupled to the scan and data lines and configured to activate the even pixels to collect image data and EMI data from the even pixels and EMI-only data from the odd pixels, and to activate the odd pixels to collect image data and EMI data from the odd pixels and EMI-only data from the even pixels, the EMI-only data from the even pixels being used to correct the image and EMI data from the odd pixels, and the EMI-only data from the odd pixels being used to correct the image and EMI data from the even pixels.

11. The system of claim 10, further comprising odd/even control circuitry coupled between the scan line and the first and second scan lines.

12. The system of claim 11, further comprising an odd/even control line coupled to the odd/even control circuitry for selectively activating the first scan line or the second scan line.

13. The system of claim 10, wherein each pixel includes a switching device and a photodetector device.

14. The system of claim 13, wherein the switching device is a FET and the photodetector device is a photodiode.

15. The system of claim 14, wherein the FET activates the photodiode to store a charge in response to a signal received by the first or the second scan line.

16. The system of claim 15, wherein the pixel communicates a signal representing charge stored within the photodiode to an associated data line after selective activation of the scan line.

17. The system of claim 10, wherein the first scan line is coupled to alternating pixels in a row, defined as the even pixels, and the second scan line is coupled to the remaining alternating pixels in the row, defined as the odd pixels.

18. The system of claim 17, wherein the odd pixels in a row are adjacent to and separated by the even pixels in the row.

19. A method for eliminating image artifacts caused by electromagnetic interference (EMI) on a digital x-ray detector comprising:

acquiring image and electromagnetic interference (EMI) signal data during an x-ray image acquisition;

activating a plurality of first scan lines coupled to even pixels in rows of a pixel array of a digital x-ray detector panel to measure the x-ray image signal of the even pixels in the rows, wherein all regions of every even pixel are used to measure the x-ray signal;

deactivating a plurality of second scan lines coupled to odd pixels in the row of the pixel array of the digital x-ray detector panel to measure the EMI signal of the odd pixels in the rows, wherein all regions of each odd pixels are used to measure the EMI signal;

removing the EMI signal from the even pixels with the measured EMI signal from the odd pixels;

activating the plurality of second scan lines coupled to the odd pixels in the rows of the pixel array of the digital x-ray detector panel to measure the x-ray image signal of the odd pixels in the rows, wherein all regions of every odd pixel are used to measure the x-ray signal;

deactivating the plurality of first scan lines coupled to the even pixels in the rows of the pixel array of the digital x-ray detector panel to measure the EMI signal of the even pixels in the rows, wherein all regions of each odd pixels are used to measure the EMI signal;

and removing the EMI signal from the odd pixels with the measured EMI signal from the even pixels.

* * * * *